(12) United States Patent
Hutchinson

(10) Patent No.: US 7,214,542 B2
(45) Date of Patent: May 8, 2007

(54) METHOD OF PROCESSING ASSAY TEST RESULTS

(76) Inventor: Michael Hutchinson, 791 Caley Rd., King of Prussia, PA (US) 19406

( * ) Notice: Subject to any disclaimer, the term of this patent is extended or adjusted under 35 U.S.C. 154(b) by 440 days.

(21) Appl. No.: 10/356,452

(22) Filed: Jan. 30, 2003

(65) Prior Publication Data

US 2004/0152208 A1    Aug. 5, 2004

(51) Int. Cl.
*G01N 21/00* (2006.01)
(52) U.S. Cl. .......................... 436/164; 436/50; 436/55; 436/514; 435/7.1; 435/7.92; 435/288.7; 422/58; 422/67
(58) Field of Classification Search ................ 436/164, 436/514, 50, 55; 435/7.1, 7.92, 288.7; 422/58, 422/67
See application file for complete search history.

(56) References Cited

U.S. PATENT DOCUMENTS

| 5,580,794 | A | * | 12/1996 | Allen ......................... 436/169 |
| 5,985,675 | A |   | 11/1999 | Charm et al. |
| 6,150,124 | A | * | 11/2000 | Riedel ......................... 435/14 |
| 6,177,281 | B1 |  | 6/2001 | Manita et al. |
| 6,268,162 | B1 | * | 7/2001 | Phillips et al. ................. 435/14 |
| 6,319,466 | B1 | * | 11/2001 | Markovsky et al. .......... 422/56 |
| 6,365,417 | B1 |  | 4/2002 | Fleming et al. |

\* cited by examiner

*Primary Examiner*—Long V. Le
*Assistant Examiner*—Jacob Cheu

(57) ABSTRACT

In accordance with certain disclosed embodiments of the present invention, there is provided a method of analyzing assay test results for determining whether a fluid under test contains a certain substance. The disclosed method includes detecting the certain substance in the fluid under test received on a test strip, and generating an electrical signal indicative of the amount of the substance detected. The disclosed method further includes responding to the signal, and determining whether or not the fluid under test contains a predetermined quantity of the certain substance to generate an electric output signal. The method disclosed also includes responding to the output signal to indicate the presence or absence of a predetermined quantity of the certain substance contained within the fluid under test. The disclosed method includes delaying in the detecting until after a predetermined time delay interval, and storing the detected information at the completion of the time delay interval. The stored information is compared with stored threshold electric signals to determine whether or not the fluid under test contains a predetermined quantity of the certain substance.

16 Claims, 4 Drawing Sheets

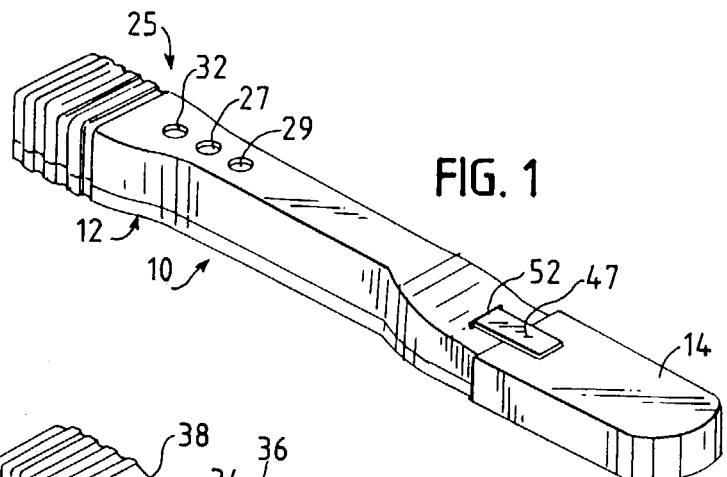
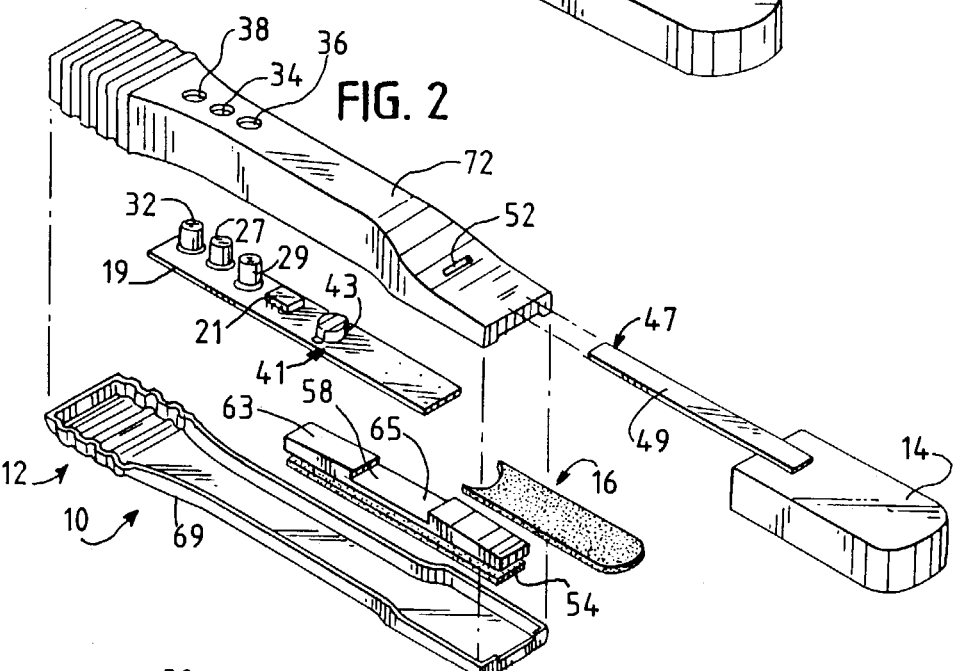
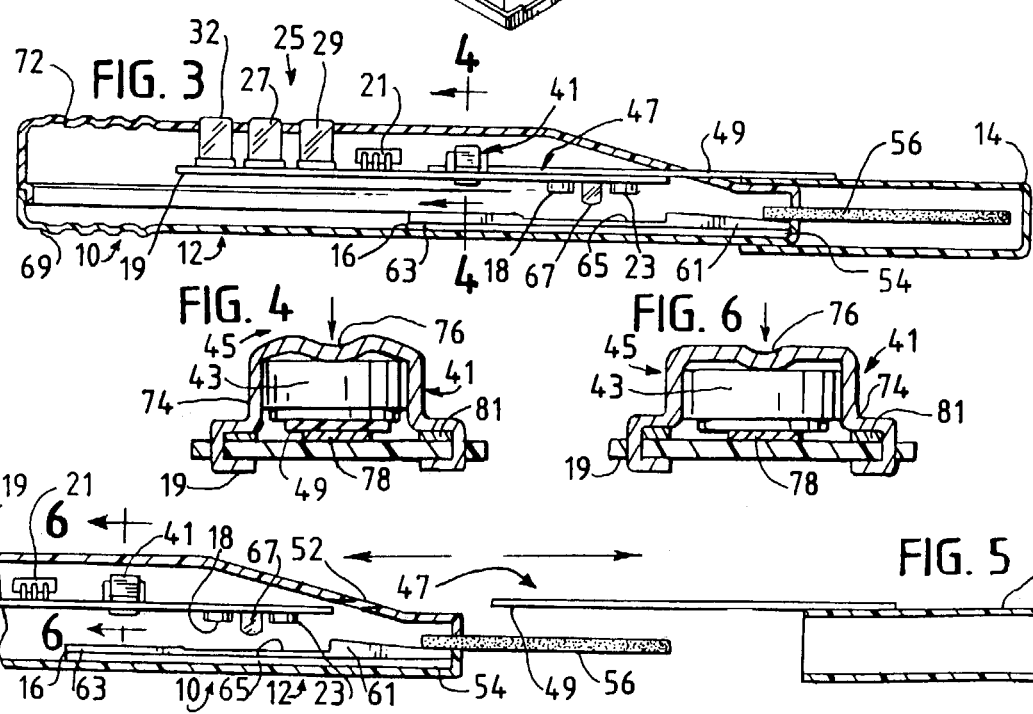

METHOD OF PROCESSING ASSAY TEST RESULTS

RELATED APPLICATIONS

This application incorporates herein by reference U.S. non-provisional patent application, entitled RAPID ASSAY STRIP AND METHOD OF RAPID COMPETITIVE ASSAY, Ser. No. 09/573,717, flled May 12, 2000, now U.S. Pat. No. 6,534,324; U.S. non-provisional patent application, entitled ASSAY TEST DEVICE AND METHOD OF MAKING SAME, Ser. No. 10/356,453, filed Jan. 30, 2003; and published European patent application, entitled DETECTION APPARATUS AND METHOD FOR THE SAME, No. EP 0,962,771A1, filed Jun. 4, 1999.

FIELD OF THE INVENTION

The present invention relates in general to a method of processing assay test results. It more particularly relates to a method of using it for assay tests, such as tests of urine samples for pregnancy, drugs of abuse, tobacco, or other.

BACKGROUND ART

There is no admission that the background art disclosed in this section legally constitutes prior art.

Assay tests have been employed to analyze test samples such as urine samples to determine whether or not they contain substances such as HCG indicating pregnancy, drugs of abuse, or other.

For example, reference may be made to the following United States patents, each of which is incorporated herein by reference:

| U.S. PAT. NO. | INVENTOR | ISSUE DATE |
| --- | --- | --- |
| 4,033,723 | Givner, et al. | Jul. 5, 1977 |
| 4,123,509 | Banik, et al. | Oct. 31, 1978 |
| 4,348,207 | Cappel | Sep. 7, 1982 |
| 4,450,239 | Chatterton | May 22, 1984 |
| 4,700,711 | Carlson | Oct, 20, 1987 |
| 5,182,216 | Clayton, et al. | Jan, 29, 1993 |
| 5,580,794 | Allen, et al. | Dec. 3, 1996 |
| 5,656,503 | May, et al. | Aug. 12, 1997 |
| 5,786,220 | Pronovost, et al. | Jul. 28, 1998 |
| 5,873,546 | Allen, et al. | Nov. 17, 1998 |
| 6,063,026 | Schauss, et al. | May. 16, 2000 |
| 6,150,178 | Cesarczyk, et al. | Nov. 21, 2000 |
| 6,235,241B1 | Catt, et al. | May 22, 2001 |

Test strips, as disclosed in one or more of the foregoing patents, are employed to receive a test sample such as a urine sample for performing an assay test. For example, a pregnancy test strip has been used to collect a urine sample to react with a reagent to produce a visible line such as a line having a pink/purple color. It is sometimes difficult to make a subjective determination as to the intensity of the color of the line relative to a comparison line. Thus, false positive indications are sometimes possible.

In an attempt to help interpret the results of such assay test, the U.S. Pat. No. 6,235,241B1 discloses a test strip disposed within a casing or housing, and uses a method of illuminating using diffusers through a test strip to help the user to interpret the results of a test. Light is sensed on the other side of the test strip by detecting light shining through the test strip. However, such a method is complex in its use, and thus relatively expensive to use.

For the purpose of providing a relatively inexpensive assay test device, which can be for single use only, as disclosed in U.S. Pat. Nos. 5,580,794 and 5,873,546, there is disclosed a method using a test membrane containing a reagent, and receiving a liquid test sample thereon. The presence of movement of the sample liquid is detected and activates the device electrically. The results of the chemical reaction of the reagent with the test sample is then sensed. In this regard, as the liquid sample moves along the test strip, the reaction is occurring and the results are sensed once the liquid reaches a certain point along the strip. Alternatively, another method is disclosed where the device may be activated electrically by closing a switch when it is removed from its pouch, and the reaction results are sensed after a specified time.

However, when the former method is used, the reaction time may be dependent on the length of time it takes for the movement of the liquid sample along the membrane. Thus, the reaction time may not be precisely controlled and repeatable, and thus accuracy may be adversely affected.

When the latter method of sensing the reaction results sometime after initially turning on the device, following a time delay, the reaction time is even less precisely controlled. There is little or no control over when the sample is first introduced to the membrane following the activation of the device, and thus the processing time could vary widely.

It is, of course, important to provide sufficient time to process the reaction. Either permitting the reaction process time to be determined by the propagation time of the sample, or by allowing the sample to be introduced at any time (even shortly before the reaction is analyzed), does not provide adequate control for the proper analysis of the reaction.

Therefore, it would he highly desirable to have a new and improved testing method, which is relatively more accurate in the determination of the test results, while at the same time being relatively inexpensive to use. Thus, such a method may, if desired, be employed for a single use, and yet be relatively accurate in its use.

BRIEF DESCRIPTION OF THE DRAWINGS

The following is a brief description of the drawings:

FIG. 1 is a pictorial view of a device which is constructed in accordance with a disclosed embodiment of the present invention;

FIG. 2 is an exploded view of the device of FIG. 1;

FIG. 3 is an enlarged sectional elevational view of the device of FIG. 1;

FIG. 4 is an enlarged sectional view of the device of FIG. 3 taken substantially on line 4—4 thereof;

FIG. 5 is a fragmentary sectional elevational view of the device of FIG. 3, illustrating it with its lid portion being removed;

FIG. 6 is an enlarged sectional view of FIG. 5 taken substantially on line 6—6 thereof;

DETAILED DESCRIPTION OF CERTAIN EMBODIMENTS OF THE INVENTION

Figure 7:
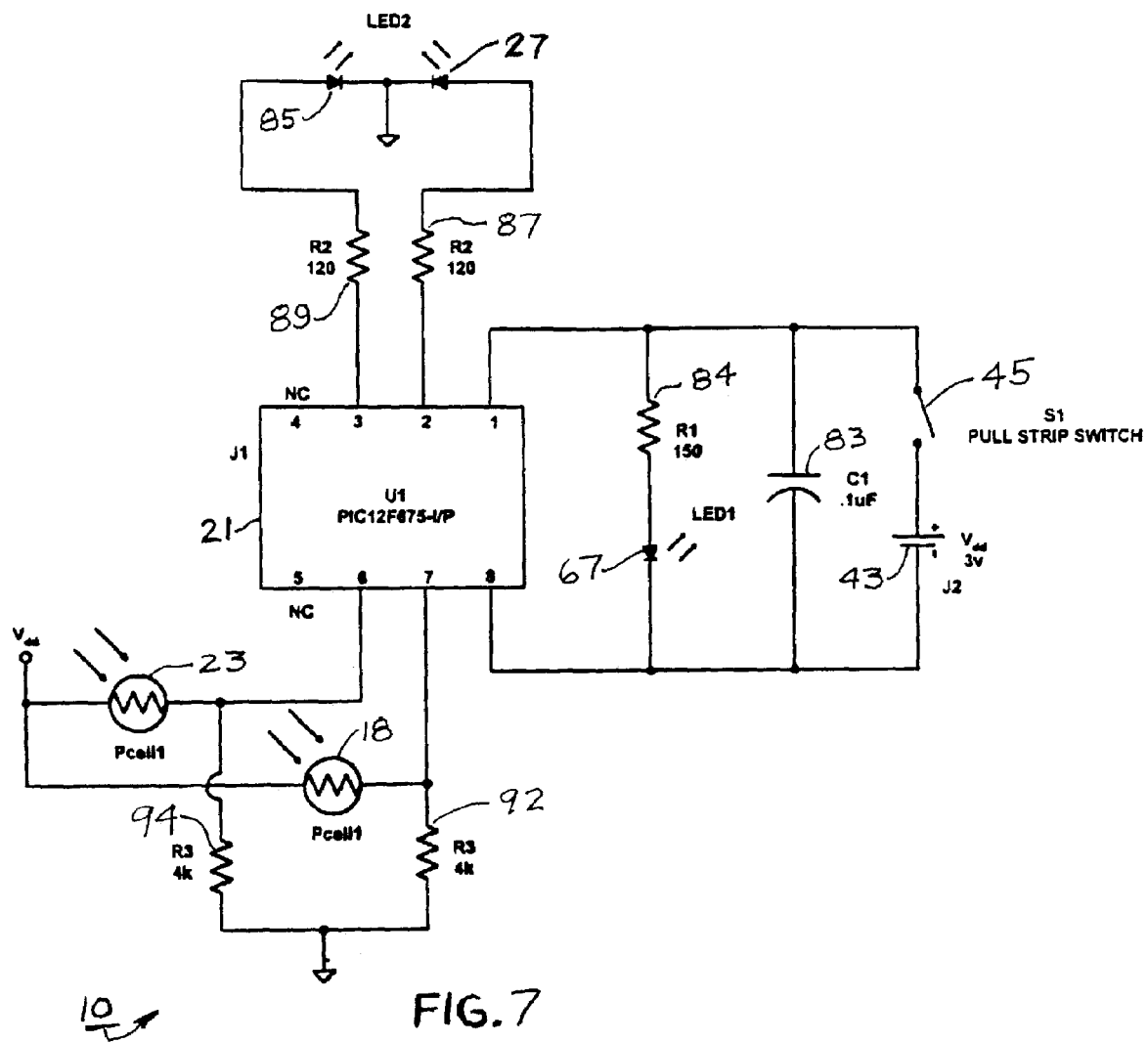
FIG. 7 is a schematic circuit diagram of the device of FIG. 1.

In accordance with certain disclosed embodiments of the present invention, there is provided a method of testing a fluid sample to determine whether or not it contains a certain substance. The disclosed method includes the starting of a timer in response to detecting the fluid sample under test being received on a test strip. The disclosed method includes causing the generation of an electric time-out signal indicative of the end of a predetermined time delay interval. Moreover, the disclosed method includes causing the determination of whether or not the fluid sample under test contains a predetermined quantity of the certain substance in response to the time-out signal. The disclosed method also includes generating an electric output signal in response to the determination, and then causing the indication of the presence or absence of a predetermined quantity of the certain substance contained within the fluid sample.

According to other methods of the disclosed embodiments of the invention, the disclosed embodiments of the methods include monitoring to determine if a power-up signal is received to start a test operation.

Referring now to the drawings, and more particularly to FIGS. 1–6 thereof, there is shown an assay test device 10, which is adapted for determining whether a fluid under test contains a certain substance, and which may be operated in accordance with a disclosed embodiment of the invention. The device 10 includes an elongated housing 12 having a removable lid or cap 14. The housing 12 is adapted to be held in the hand of the user.

An elongated test strip 16 is disposed longitudinally within the housing 12. The test strip may be in the form of the test strip disclosed in the aforementioned European patent application No. EP0,962,771A1. The test strip 16 of the device 10 is initially contemplated to be used for pregnancy testing, but it is to be understood by those skilled in the art, that other different types and kinds of test strips may be employed for other testing purposes, including but not limited to, the testing for drugs of abuse, and other tests.

A sample sensor 18 (FIGS. 3 and 5) is mounted on the underside of a printed circuit board 19 and is disposed opposite the test strip 16 intermediate its end portions for detecting the presence of the sample as it flows along the test strip for generating a signal indicative of the presence of the sample. The sample sensor may be a photo-optic sensor, but it can be other types and kinds of sensors, including magnetic sensors such as Hall effect device.

A processor 21 mounted on the top surface of the printed circuit board 19 is responsive to the sample presence signal from the sample sensor 18 for starting a software timer to generate a time delay interval and for generating a time-out signal at the end if the interval. In this regard, the time delay interval allows for the propagation time of the sample from one end portion to an intermediate portion of the test strip 16 opposite the sensor 18.

As shown in FIGS. 3 and 5, a reaction sensor 23 mounted on the underside of the printed circuit board 19 responds to the time-out signal from the processor 21 for detecting a certain substance in the fluid under test received on the test strip 16 to generate an electrical signal indicative of the amount of the substance detected. In this regard, the reaction sensor is preferably a photo-optic sensor, but it may also be other types and kinds of sensors, including magnetic sensors such as Hall effect devices. When a photo-optic sensor is used, and when the test strip 16 is employed as disclosed in the aforementioned European patent application, a dark line forms on the test strip and is detected by the photo-optic reaction sensor 23.

As indicated in FIGS. 1 and 3, a display generally indicated at 25 includes an amber light emitting diode (LED) 27, a green light emitting diode (LED) 29 and a red light emitting diode (LED) 32 disposed in a row on the top surface of the housing 12, and are positioned within corresponding holes 34, 36 and 38. The display 25 responds to an output signal from the processor 21 for indicating the presence or absence of a predetermined quantity of the certain substance contained within the fluid under test. The processor generates the output signal in response to the signal from the reaction sensor 23. The output signal from the processor is indicative of the presence or absence of at least a predetermined quantity of the substance contained in the sample.

A power supply generally indicated at 41 is mounted on the top surface of the printed circuit board 19, and is preferably in the form of a battery 43 which is connected electrically to the printed circuit board 19 and its components via a switch generally indicated at 45 (FIGS. 4 and 6). A switch actuator 47 preferably in the form of an insulator strip 49 extends through an opening 52 in an angular wall portion of the housing 12 and extends to the switch 45 when the lid 14 is assembled to the housing 12 as shown in FIGS. 1 and 3. When the lid 14 is removed from the housing 12 as indicated in FIG. 5, the actuator 47 is pulled away from the switch 45 as indicated in FIGS. 4 and 6, to cause the battery 43 to be connected electrically to the printed circuit board 19 for energizing the device 10.

In use, in order to start a testing operation by, for example, testing for HCG in a urine sample to indicate whether or not a person is pregnant, the lid 14 is removed from the housing 12 to cause the insulation strip 49 to be pulled out from under the battery 43 to cause the battery to energize the device 10. Once energized, the device 10 causes the amber LED 27 to blink or otherwise to turn on, indicating that the power is on and the device 10 is ready to receive the urine test sample. Should the device not be used after being energized, the amber LED 27 blinks or stays on until the battery becomes exhausted.

The user then applies a urine sample to the test strip 16.

The sample sensor 18 detects the presence of the urine sample once it has migrated along the test strip and the top surface of the test strip turns from a white color to a darker color as a result of being wetted by the urine sample. If the sensor 18 does not respond to the color change, the device 10 does not proceed further in the operation and eventually the battery 43 will become exhausted.

The processor 21 causes a software timer to start a time delay interval with the actuation of the battery 43 and will stop timing once the sample sensor 18 detects the presence of the urine sample, or the timer times out. If the timer times out prior to the sensing of urine sample, the amber LED 27 will start to blink to provide a visual indication that the battery life is near its end.

If the sample sensor 18 detects the presence of the urine sample (even after the amber light commences blinking), the processor 21 responds to an electrical signal from the sample sensor 18 to start another time delay interval based on the performance/optimization of the desired test. In this regard, the time interval is provided to allow sufficient time for the test to develop. For example, for a pregnancy test, there may be a time-out interval of 3 minutes.

Once the processor 21 reaches the end of the time-out interval, the processor 21 causes the reaction sensor 23 to read the intermediate portion of the test strip 16 to detect the presence of a line created by the test reaction. The current value is compared with a stored value of the intensity of the line to determine whether or not the line is present. If the difference is greater than the defined threshold level, the green LED 29 is illuminated, to indicate a positive test result. If the difference is less than the threshold value, the red LED 32 is illuminated by the processor, to indicate a negative test result. Either the green LED 29 or the red LED 32 remains illuminated until the battery dies, or the battery 43 is disconnected from the printed circuit board 19 by means of the switch actuator 47 engaging the switch 45 by replacing the lid 14 on the housing 12.

It is to be understood that the device 10 is contemplated to be a single use device which is relatively accurate in its measurements. However, it will be understood by those skilled in the art that the device 10 may be a multiple use device by permitting the test strip to be replaced with a fresh test strip.

Considering now the test strip 16 in greater detail with reference to FIGS. 3 and 5 of the drawings, the test strip 16 includes a backing strip 54 which has a sample pad or wick 56 extends out of the housing 18 and is covered by the lid 14 when it is assembled to the housing 12. When the lid 14 is removed from the housing 12, the wick 56 is exposed so that the urine sample may be applied thereto. A porous carrier strip 58 has a reagent section or pad 61 affixed to the wick 56, and a fluid absorption section or strip 63 at the opposite end portion thereof. A catching section or line forming zone 65 on the upper surface of the intermediate portion of the porous carrier strip 58 is disposed opposite the reaction sensor 23 where a line is formed once the reaction occurs when human chorionic gonadotropin (HCG) is present in the urine sample indicating that the user is pregnant.

The reagent pad 61 contains the suitable reagent for performing the desired test on the sample. In this regard, the sample is received on the wick 56 and migrates through the reagent pad 61 to the intermediate portion of the carrier strip 58 until the sample sensor 18 disposed opposite the intermediate portion of the carrier strip 58 detects the presence of the sample due to the change in color of the wetted porous carrier strip 58. In this regard, an illuminating light-emitting diode (LED) 67 disposed on the underside of the printed circuit board 19 between the sensors 18 and 23 illuminate the intermediate portion of the porous carrier strip 58 to reflect light therefrom to the sensors. The LED 67 may produce light in the visible range of the electromagnetic spectrum. A white LED is preferred, but a green LED may also be used for the illuminating LED 67, depending on the color of the line formed on the test strip 16.

Thus, in the present example, as a pregnancy test, no control line is required. Additionally, the reaction forms a complex produced by bonding between a white latex particle and a marking element in the form of colloidal gold to the antigen HCG.

Considering now the housing 12 in greater detail, the housing 12 includes a bottom portion 69, which is secured to a top portion 72 for enclosing the printed circuit board 19 with its components as well as the test strip 16. When the device 10 is employed as a multiple use device, the housing 12 can be disassembled as indicated in FIG. 2 to permit the test strip 16 to be replaced by a fresh test strip for performing additional tests. The insulator strip 49 of the switch actuator 47 may be in the form of a rigid strip of suitable materials such as thermal plastic or other such material. In this regard, the insulator strip 49 can be reinserted through the opening 52 and under the battery 43 to disengage it electrically from the printed circuit board 19.

Considering now the switch actuator 47 with reference to FIGS. 4 and 6 of the drawings, the actuator 47 includes a u-shaped spring mounting device 74 which serves as a conductor and surmounts the battery 43 and positions it opposite to a circuit board negative contact 78. The top portion of the mounting device or contact 74 is dimpled at 76 to engage the positive surface of the battery 43 electrically to provide electrical contact between the positive terminal of the battery 43 and a positive terminal 81 on the printed circuit board 19. The insulator strip 49 is adapted to be positioned between the negative terminal of the battery 43 and the circuit board contact 78 as shown in FIG. 4 to disengage electrically the battery 43 from the printed circuit board 19. When the lid 14 is removed, the insulator strip 49 is fixed at one of its ends to the lid 14 and its opposite end is pulled out from between the underside of the battery 43 and the circuit board contact 78. This causes the battery 43 to have its negative terminal snap into engagement with the contact 78 due to the spring tension of the spring mounting device 74.

Considering now the electrical circuit for the device 10 with reference to FIG. 7, when the switch 45 is closed by removing the strip 47, the battery 43 is connected across a capacitor 83, and a parallel combination with the illuminating LED 67 connected in series with a current limiting resistor 84 so that the LED 67 becomes illuminated once the switch 45 is closed. This current flow is sensed by the processor 21 to cause the amber LED 27 to be energized via a current limiting resistor 87. In the actual implementation of the circuit as shown in FIG. 7, it is preferred to use a tri-color light-emitting diode (LED) 85 to form the green and red colors corresponding to the green LED 29 and the red LED 32 of FIG. 1. The LED 85 is energized via a current limiting resistor 89 by the processor 21.

The sensors 18 and 23 in the form of photo-optic photo cells are connected via a voltage divider network including resistors 92 and 94 to provide the threshold levels for the photo cells so that the photo cells will not respond to a change in color unless it exceeds the threshold level so that the device 10 can detect a sufficient amount of the certain substance contained in the test sample.

The following is a list of components which may be used in connection with the disclosed embodiment shown in FIG. 7:

| | P |
|---|---|
| S1 | 1/4" W × 2" L × .010" H, INSULATION STRIP |
| Vcc | PANASONIC PT #CR1220, LITHIUM COIN BATTERY |
| J2 | KEYSTONE PT #3001, THRU HOLE MOUNT COIN CELL RETAINER |
| PCELL1 | PERKINELMER PHOTOCONDUCTIVE CELL PT #VT90N1 |
| R3 | 4K OHM CARBON FILM RESISTOR, 1/4 WATT, 2%, AXIAL LEAD |
| R2 | 120 OHM CARBON FILM RESISTOR, 1/4 WATT, 5%, AXIAL LEAD |
| R1 | 150 OHM CARBON FILM RESISTOR, 1/4 WATT, 5%, AXIAL LEAD |
| C1 | 0.1 uf CAPACITOR, 50 V, 10%, CERAMIC, AXIAL LEAD |
| LED2 | LUMEX PT #SSL-LX5099IGW, T-5 mm (T-1 3/4) RED/GRN BICOLOR LED |
| LED1 | LUMEX PT #SSL-LX3044GD, T-3 mm (T-1) 565 nm GRN LED |
| J1 | DUAL-IN-LINE SOCKET, 8 PIN, OPEN FRAME, TIN LEADS |
| U1 | MICROCHIP PT #PIC12F675-I/P MICROCONTROLLER |

Figure 8:
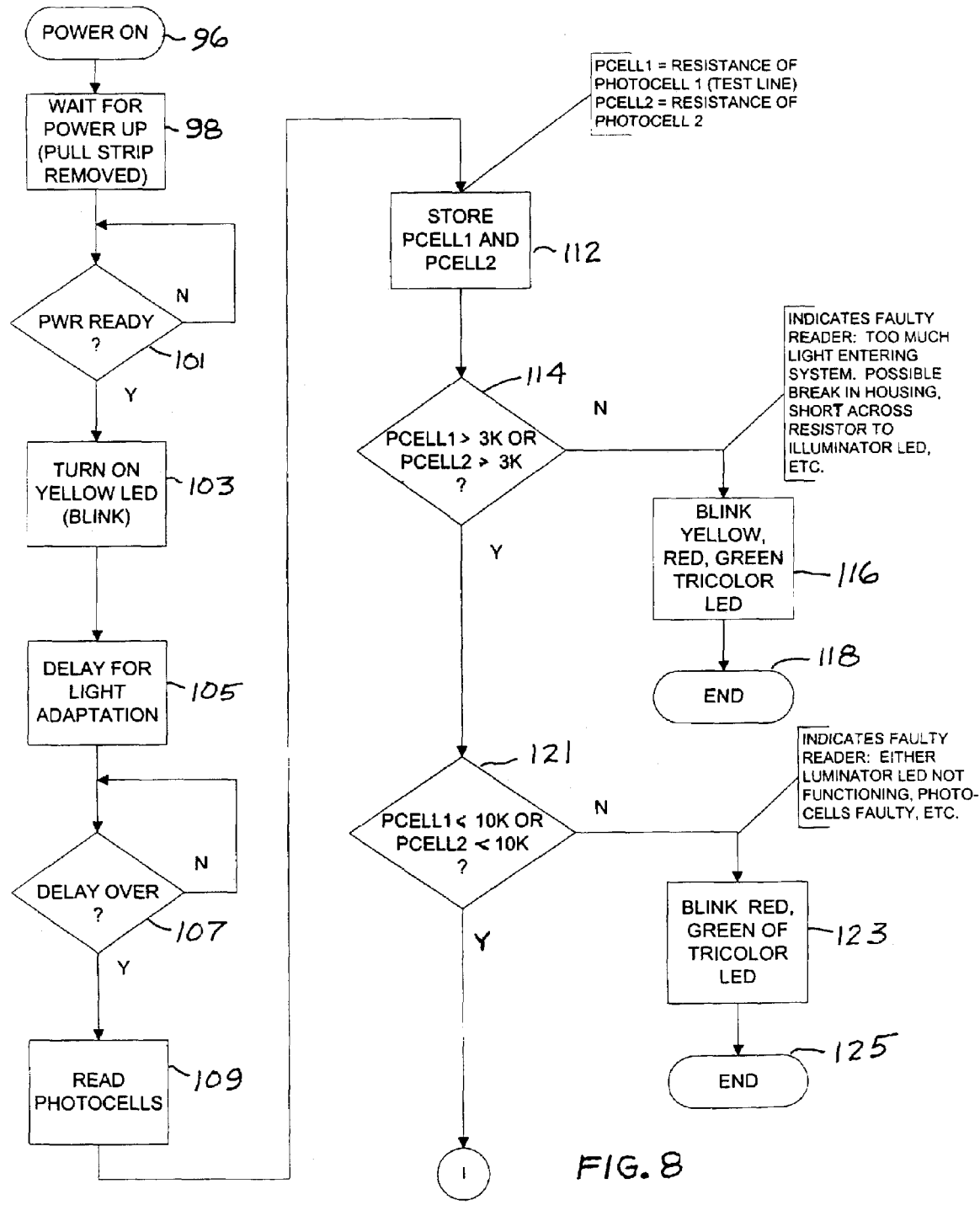
FIGS. 8 and 9 are flow chart diagrams of the software or firmware.
Figure 9:
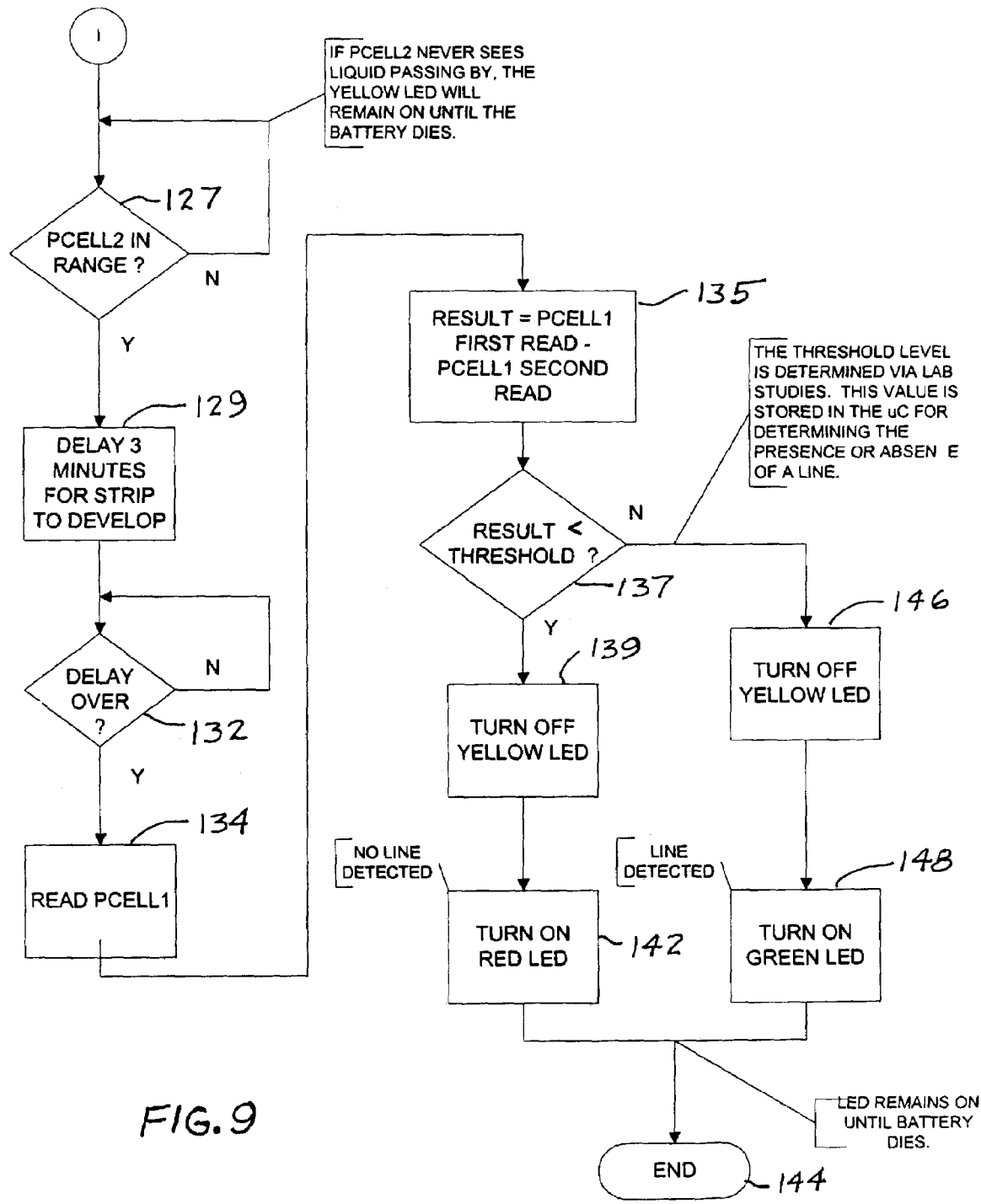

Referring now to FIGS. 8 and 9 of the drawings, the method of the disclosed embodiment of the present invention will now be described in greater detail. As indicated at box 96, the powering on of the device 10 will now commence. At box 98, the software or firmware for the processor waits for the power up operation to commence when the insulation strip is removed from the battery by pulling the lid 14 from the housing 12. As indicated at box 101, the processor makes a determination as to whether or not the powering on of the device 10 is ready. If the closing of the switch to the battery has not taken place to produce a power-on signal, the software continues to monitor for the power being ready.

Once the lid 14 is removed to cause the power-on signal to be generated, a transition is made to box 103, whereby the yellow or amber light emitting diode is turned on to illuminate it.

At box 105, a time delay interval commences to allow the light adaptation for the photo-cell sensors. As indicated at box 107, the software continues to monitor the light adaptation delay. If the delay is not completed, it loops back to continue to monitor.

Once the light adaptation delay is completed, a transition occurs to box 109 where the photo-cell sensors (the sample sensor and the reaction sensor) are read to initialize the system. As indicated at box 112, the information read from the photo-cell sensors is stored in the memory of the processor.

As indicated at decision box 114, a determination is made as to whether or not the photo-cell sensor readings are less than 3,000 ohms. If either one is less than 3,000 ohms, as indicated at box 116, the amber LED, or if a tri-color LED is used, all three colors are illuminated and begin to blink. This blinking light indicates a faulty reader. For example, excessive light may be entering the system. Also, there may be a possible break in the housing, or a short circuit across a resistor to the illuminator LED, or other such problem may exist. In such case, the operation then ends at box 118.

Alternatively, if both of the photo-cell sensor readings are greater than 3,000 ohms, then a decision is made at box 121 as to whether or not the photo-cell sensor readings are greater than 10,000 ohms. If they are greater than 10,000 ohms, then there may be a faulty reader. In this regard, either the illumination LED is not functioning, or the photo-cell sensors are faulty, or other such problem. As indicated in box 123, if a tri-color LED is used, the read and green of the tri-color LED are illuminated. If individual LED devices are employed, then the red and the green are illuminated simultaneously to indicate the end of the operation as indicated at box 125.

Alternatively, if the measurements are less than 10,000 ohms, then the operation proceeds to box 127 (FIG. 9). At that decision box, it is determined if the photo-cell 2 (the sample sensor) is in range or not. If the photo-cell sample sensor fails to see the liquid passing by on the test strip, the yellow LED remains on until the battery dies. If the photo-cell sample sensor is in range, then the operation transitions to box 129 where the predetermined time delay interval commences to permit the test strip to develop the reaction. In the disclosed embodiment, the predetermined time delay interval is at 3 minutes. A decision box 132 monitors the delay to determine whether or not the delay has completed. Once it is completed, the operation transitions to box 134 where the photo-cell reaction sensor (photo-cell 1) is read.

As indicated at box 135, the reading of the reaction sensor information is subtracted from the initial reading of the reaction sensor photo-cell. As indicated at box 137, a determination is made as to whether or not the result is less than the threshold. If it is greater than the threshold, then the yellow LED is turned off at box 146 and the green LED is turned on at box 148 to indicate that a line has been detected at the test strip indicating that the reaction has a positive indication, such as an indication of pregnancy. The result is greater than the threshold when a reaction line is present, because the color of the line is such that there is less reflection of light. The box 148 then transitions to the end box 144 where the LED remains on until the battery dies.

Alternatively, if the result is less than or equal to the threshold, then the transition from the box 137 is to the box 139 to turn off the yellow LED 139 and turn on the red LED 142 indicating that no line has been detected for a negative indication. When no dark line is present, then the reflected light is equal to or less than the threshold measurement of reflected light. From there, the transition is to the end box 144 where the red LED remains on until the battery dies.

As will become apparent to those skilled in the art, numerous modifications as well as variations of the disclosed embodiments of the present invention may be made in light of the foregoing teachings. Therefore, it is to be understood that within the scope of the appended claims, the invention may be practiced otherwise as specifically described herein.

What is claimed is:

1. A method of testing a fluid sample to determine whether or not it contains a certain substance, comprising:
    using an assay test device having sample and reaction sensors mounted within a housing;
    storing a predetermined threshold range for readings of the sample and reaction sensors indicative of a desired amount of light within the housing prior to introduction of the fluid sample;
    using the sample sensor to determine an initial sample sensor reading;
    using the reaction sensor to determine an initial reaction sensor reading;
    storing the initial readings of the sample and reaction sensors;
    comparing the initial sample sensor reading to the predetermined threshold range;
    determining in response to the comparing the initial sample sensor reading to the predetermined threshold range whether or not the initial sample sensor reading is acceptable;
    comparing the initial reaction sensor reading to the predetermined threshold range;
    determining in response to the comparing the initial reaction sensor reading to the predetermined threshold range whether or not the initial reaction sensor reading is acceptable;
    generating a signal in response to either determining step finding an unacceptable initial reading to alert the user that the test device is faulty;
    flowing the fluid sample along an elongated test strip;
    using the sample sensor spaced from the test strip to detect the presence of the fluid sample using the light reflecting from a first location on the test strip;
    starting a timer for a predetermined time delay interval in response to the sample sensor detecting the fluid sample under test being received at the first location on the test strip;
    generating an electric time-out signal at the end of the predetermined time delay interval started by the sample sensor;
    using the reaction sensor remote from the sample sensor starting the time delay interval for detecting the fluid sample under test at a second location on the test strip in response to the time-out signal at the end of the time delay interval started by the sample sensor;
    determining whether or not the fluid sample under test at the second location on the test strip contains a predetermined quantity of the certain substance in response to the reaction sensor detecting the fluid sample under test;

generating an electric output signal in response to the determination in the reaction sensor; and indicating the presence or absence of a predetermined quantity of the certain substance contained within the fluid sample under test, wherein the sample sensor and the reaction sensor are photo-optic sensors.

2. The method according to claim 1, wherein said timer is a software timer.

3. The method according to claim 1, wherein said time delay interval is about three minutes.

4. The method according to claim 1, wherein said determining step in response to reaction sensor for a predetermined quantity of the certain substance includes initiating a photo optic sensing of the results of a reaction on the test strip.

5. The method according to claim 1, wherein said indicating step includes initiating the illumination of a light source.

6. The method according to claim 5, wherein said light source is at least one light emitting diode.

7. The method according to claim 1, further including monitoring to determine if a power up signal is received to start a test operation.

8. The method according to claim 7, further including illuminating a light source indicating that the test is ready to commence.

9. The method according to claim 8, wherein said illumination changes to a blinking mode after a predetermined time delay interval indicating that the test sample should be introduced to the test strip prior to exhaustion of a battery.

10. The method according to claim 7, further including initially reading the sample sensor and the reaction sensor after a light adaptation time interval for threshold determination purposes.

11. The method according to claim 1, further including determining whether the sample sensor readings exceeds a predetermined threshold.

12. The method according to claim 1, further including determining whether the reaction sensor readings exceed a predetermined reaction sensor threshold.

13. The method according to claim 11, further including starting the timer when it is determined that the sample sensor readings exceed the predetermined sample sensor threshold.

14. The method according to claim 12, further including determining whether or not the fluid under test contains a predetermined quantity of the certain substance after the determination is made of the reaction sensor readings exceed the reaction sensor threshold.

15. The method according to claim 14, further including illuminating at least one light source indicating a positive test result in response to the reaction sensor determination.

16. The method according to claim 14, further including illuminating at least one light source indicating a negative test result in response to the reaction sensor determination.

* * * * *